United States Patent [19]

Jeppsson

[11] Patent Number: 5,028,600

[45] Date of Patent: Jul. 2, 1991

[54] NOVEL PHARMACEUTICAL COMPOSITION

[75] Inventor: Roland I. Jeppsson, Stockholm, Sweden

[73] Assignee: KabiVitrum AB, Sweden

[21] Appl. No.: 316,576

[22] Filed: Feb. 28, 1989

Related U.S. Application Data

[63] Continuation of Ser. No. 12,699, Feb. 9, 1987, abandoned.

[30] Foreign Application Priority Data

Feb. 13, 1986 [SE] Sweden ................................ 8600632

[51] Int. Cl.$^5$ ............................................. A61K 31/56
[52] U.S. Cl. ..................................... 514/182; 514/180
[58] Field of Search ................................ 514/180, 182

[56] References Cited

U.S. PATENT DOCUMENTS

| | | | |
|---|---|---|---|
| 3,163,578 | 12/1964 | Bruckner et al. | 167/74 |
| 3,647,829 | 3/1972 | Kruger | 260/297.4 |
| 3,900,561 | 8/1975 | Davis et al. | 514/179 |
| 3,917,830 | 11/1975 | Davis et al. | 514/178 |
| 4,168,308 | 9/1979 | Wretlind et al. | 514/626 |
| 4,340,594 | 7/1982 | Mizushima et al. | 514/180 |

Primary Examiner—Frederick E. Waddell
Assistant Examiner—Kimberly Jordan
Attorney, Agent, or Firm—Pollock, Vande Sande & Priddy

[57] ABSTRACT

A composition for intravenous administration of 3-alpha-hydroxy-5-beta-pregnan-20-one (pregnanolone), comprising a stable oil-in-water emulsion, capable of being sterilized by autoclaving, of from 0.1 to 1.0 g of pregnanolone.

14 Claims, No Drawings

NOVEL PHARMACEUTICAL COMPOSITION

This application is a continuation of U.S. Pat. No. 012,699, filed on Feb. 9, 1987, now abandoned.

FIELD OF THE INVENTION

The present invention relates to a novel pharmaceutical composition for intravenous administration comprising 3alphahydroxy5beta-pregnan-20-one, in the following referred to as pregnanolone as active ingredient.

BACKGROUND OF THE INVENTION

It has long been known that a number of steroids have pharmacological effects as anesthetics. Reference is made e.g. to Selye, Anesthetic effects of steroid hormones, Proc Soc Exp Biol Med Vol 46, 116–121 (1941). However, many such components which have been tested have proved to suffer from undesirable properties causing side effects which have prevented clinical use of the steroids studied. The solubility characteristics of such compounds have caused problems which have proved difficult to overcome. In particular, many of these compounds are highly lipophilic, which has contributed greatly to the problems in preparing stable, clinically useful formulations for intravenous use.

The anesthetic properties of pregnanolone were first described by Figdor et al, Central activity and structure in a series of water-soluble steroids, J Pharm Exp Therap Vol 119, 299–309 (1957). In this paper, the aim was to overcome the administration-detoxification problem of the known steroids with anesthetic activity by conversion to water-soluble ester derivatives, which thus would be suitable for intravenous administration (Figdor et al loc cit p 300). The substances were tested in aqueous suspension containing methyl cellulose as suspending agent. However, the results were not successful.

Gyermek, in his paper "Pregnanolone: A Highly Potent, Naturally Occurring Hypnotic-Anesthetic Agent" Proc Soc Exp Biol Med Vol 125, 1058–1062 (1967) described animal studies using pregnanolone dissolved in propylene glycol. Since such preparations are not suitable for clinical use, no suggestions are given how to solve the problem of obtaining pregnanolone in a clinically acceptable and stable administration formula.

Three steroids have been used clinically as anesthetics, but none of these is currently being used. The compound 21-hydroxypregnan-3,20-dione, also known as hydroxydione and under the trade name Viadril, was introduced in 1955. Reference is made to Laubach et al, Steroid anesthetic agent, Science Vol 122, 78 (1955). Because of several disadvantages it was withdrawn. The compound 3alphahydroxy-5alpha-pregnan-11,20-dione, was put on the market under the trade name Althesin. Reference is made to Atkinson et al, Action of some steroids on the central nervous system of the mouse, J Med Chem Vol 8, 426–432 (1965), and to British patent specifications 1317184 and 1379730. This substance was brought into solution by adding the less active 21-acetate and a co-solvent, a non-ionic surface active polyoxyethylated castor oil available under the trade name Cremophor-EL. Also this steroid product was, however, withdrawn because of serious side effects.

The third steroid anesthetic product, minaxolone, was subjected to clinical evaluation in 1979. It was withdrawn because of problems with its toxicology profile.

In summary, the original screening studies in experimental animals, from which studies the animals were not allowed to survive were carried out using three types of pharmaceutical formulations:

1. ex tempore solutions in warm peanut or sesame oil which were injected as supersaturated solutions after being cooled to body temperature and sometimes containing a precipitate of crystalline material,
2. ex tempore aqueous suspensions prepared in roller mills with cellulose derivatives as thickening agents,
3. solutions in tissue irritating propylene glycol.

The exploratory synthetic chemistry which followed these studies was directed towards derivatives such as acetates, semisuccinates having higher water solubility than the parent compounds and also having the ability to form sodium salts. These derivatives must be hydrolyzed by the body before exerting the clinical effect, giving an unacceptable slow onset of action.

As described above this direction of research did not result in clinically acceptable formulations.

There is accordingly a great need for a clinically useful effective steroid anesthetic product which can be brought into an administration formula which is stable and suitable for intravenous administration. The present invention provides such a composition comprising an emulsion of pregnanolone.

DETAILED DESCRIPTION OF THE INVENTION

The present invention provides a novel, clinically useful and pharmaceutically acceptable composition for intravenous administration comprising pregnanolone as active ingredient.

The novel composition is capable of withstanding sterilization by autoclaving, which is an important advantage. The novel compositions of the invention comprise in a general sense, pregnanolone in an amount of from 0.1 to 1.0 g per 100 ml in a lipid oil-in-water emulsion, where the active substance is substantially dissolved in the oil phase. More particularly, the novel emulsion of the invention comprises:

a) pregnanolone in an amount of from 0.1 to 1.0 g per 100 ml of the final composition p b) a lipoid in an amount of from 10 to 30 g per 100 ml of the final composition, said lipoid being selected from coconut oil, borago oil, safflower oil, cotton seed oil, soybean oil, and synthetic-type structured glyceride lipid which contains a mix of long chain and medium chain fatty acids in the molecule c) an emulsifying agent in an amount of from 1 to 5 g per 100 ml of the final composition, said emulsifying agent being selected from egg yolk phospholipids and soya phospholipids d) water for injection e) glycerol to isotonicity of the final composition.

If desired, also the following components may be added:

f) acetylated monoglycerides in an amount of from 0 to 20, preferably from 5 to 10, g per 100 ml of the final composition g) cholesterylhemisuccinate, in an amount of from 0.01 to 0.2 g per 100 ml of the final composition.

The amount of pregnanolone is preferably from 0.3 to 0.8 and principally from 0.4 to 0.5 g per 100 ml of the final composition.

The amount of lipoid is preferably from 15 to 20 g per 100 ml of the final composition. The lipoid is pharmacologically inert.

The amount of actetylated monoglycerides, if present, is preferably from 5 to 10 g per 100 ml of the final composition.

The amount of glycerol is such as to give an isotonic final composition, which means an amount of from 1.0 to 2.5 g glycerol per 100 ml of the final composition.

For preparing the novel oil-in-water emulsion of present invention, it is suitable to dissolve, in a first step, the active substance, pregnanolone, in the lipoid. The resulting solution is then emulsified by means of conventionally used high pressure homogenizers, in an aqueous medium comprising water for injection, emulsifying agent, and glycerol as specified above and, if desired, acetylated monoglycerides and cholesterylhemisuccinate. In the resulting emulsion, the particle size of the oil droplets will be less than 5 $\mu$, with a large part less than 1 $\mu$. The average size of the oil droplets will be less than 1 $\mu$, preferably from 0.2 to 0.3 $\mu$.

The novel, intravenously injectable, composition of the invention will accordingly essentially comprise a solution of pregnanolone in the lipoid component as hydrophobic phase, which hydrophobic phase is emulsified in a hydrophilic phase.

The composition of the invention is further illustrated by the following examples:

EXAMPLE 1

An oil-in-water emulsion of pregnanolone was prepared from the following components:

| | |
|---|---|
| Pregnanolone | 0.4 g |
| Egg yolk phospholipids | 1.8 g |
| Soybean oil | 20.0 g |
| Acetylated monoglycerides | 7.0 g |
| Glycerol | 1.7 g |
| Water for injection | to 100 ml |
| pH was adjusted to 7.7 with 1 M sodium hydroxide. | |

In a first step, pregnanolone was mixed with the soybean oil, resulting in substantial dissolution therein. An emulsion was then prepared from the resulting pregnanolone-soybean oil composition, together with the additional indicated components. The resulting emulsion was stable and had an average particle size of from 0.2 to 0.3 $\mu$ and could be sterilized by autoclaving without decomposition.

EXAMPLES 2-4

An oil-in-water emulsion of pregnanolone was prepared as described in Example 1 with the following components:

| Component | Example 2 | Example 3 | Example 4 |
|---|---|---|---|
| Pregnanolone | 0.4 g | 0.4 g | 0.4 g |
| Egg yolk phospholipids | 2.4 g | 3.6 g | 3.6 g |
| Soybean oil | 20.0 g | 20.0 g | 15.0 g |
| Acetylated monoglycerides | 7.0 g | — | — |
| Glycerol | 1.7 g | 1.7 g | 1.7 g |
| Water for injection | to 100 ml | to 100 ml | to 100 ml |
| pH adjusted with 1 M sodium hydroxide to a value of | 7.7 | 8.0 | 7.5 |

EXAMPLE 5

An oil-in-water emulsion of pregnanolone according to Example 2 was prepared with the difference that 0.05 g cholesterylhemisuccinate per 100 ml of the final composition was also included in the emulsion.

EXAMPLE 6

An oil-in-water emulsion of pregnanolone according to Example 1 was prepared with the following components:

| | |
|---|---|
| Pregnanolone | 0.4 g |
| Egg yolk phospholipids | 1.2 g |
| Soybean oil | 20.0 g |
| Acetylated monoglycerides | 7.0 g |
| Glycerol | 1.7 g |
| Cholesterylhemisuccinate | 0.1 g |
| Water for injection | to 100 ml |
| pH adjusted with 1 M sodium hydroxide to a value of | 7.8 |

EXAMPLE 7

An oil-in water emulsion of pregnanolone was prepared as described in Example 1 with the following components:

| | |
|---|---|
| Pregnanolone | 0.4 g |
| Egg yolk phospholipids | 2.4 g |
| Borago oil | 20.0 g |
| Acetylated monoglycerides | 7.0 g |
| Glycerol | 1.7 g |
| Water for injection | to 100 ml |
| pH adjusted with 1 M sodium hydroxide to a value of | 7.7 |

EXAMPLE 8

An oil-in-water emulsion of pregnanolone according to Example 7 was prepared with the difference that 0.05 g cholesterylhemisuccinate per 100 ml of the final composition was also included in the emulsion.

EXAMPLE 9

An oil-in-water emulsion of pregnanolone was prepared as described in Example 1 with the following components:

| | |
|---|---|
| Pregnanolone | 0.4 g |
| Egg yolk phospholipids | 2.4 g |
| Safflower oil | 20.0 g |
| Acetylated monoglycerides | 7.0 g |
| Glycerol | 1.7 g |
| Water for injection | to 100 ml |
| pH adjusted with 1 M sodium hydroxide to a value of | 8.0 |

EXAMPLE 10

An oil-in-water emulsion of pregnanolone was prepared as described in Example 1 with the following components:

| | |
|---|---|
| Pregnanolone | 0.4 g |
| Egg yolk phospholipids | 2.4 g |
| Cotton seed oil | 20.0 g |
| Acetylated monoglycerides | 7.0 g |
| Glycerol | 1.7 g |

| | |
|---|---|
| Water for injection | to 100 ml |
| pH adjusted with 1 M sodium hydroxide to a value of | 7.9 |

EXAMPLE 11

An oil-in-water emulsion of pregnanolone according to Example 10 was prepared with the difference that no acetylated monoglycerides were included in the emulsion.

The emulsions according to examples 2–11 were stable and had an average particle size as obtained according to Example 1 and could withstand sterilization by autoclaving. Upon intravenous administration to test animals, they produced the desired anesthetic effect without giving rise to any serious side effects.

What we claim is:

1. A composition for intravenous administration of 3alphahydroxy-5beta-pregnan-20-one (pregnanolone), comprising a stable oil-in-water emulsion capable of being sterilized by autoclaving wherein the average size of the oil particles is less than 1 μ and which comprises calculated per 100 ml of the final composition:
    a) pregnanolone in an amount of from 0.1 to 1.0 g;
    b) a lipoid in an amount of from 10 to 30 g, selected from the group consisting of coconut oil, borago oil, safflower oil, cotton seed oil, soybean oil, and structured glyceride lipid which contains a mix of long chain and medium chain fatty acids in the molecule;
    c) an emulsifying agent in an amount of from 1 to 5 g, selected from egg yolk phospholipids and soya phospholipids;
    d) water for injection;
    e) glycerol to give isotonicity to the final composition.

2. A composition according to claim 1 comprising calculated per 100 ml of the final composition:
    a) 0.4 grams of pregnanolone
    b) 1.8 grams of egg yolk phospholipids
    c) 20.0 grams of soybean oil
    d) 7.0 grams of acetylated monoglyceride
    e) 1.7 grams of glycerol
    f) water to make 100 ml 3. The composition of claim 2 wherein the pH is 7.7.

4. The composition according to claim 1, further comprising acetylated monoglycerides in an amount of from 0 to 20 g.

5. A composition according to claim 4, further comprising cholesterylhemisuccinate in an amount of from 0.01 to 0.2 g.

6. A composition according to claim 1, comprising, calculated per 100 ml of the final composition:
    a) pregnanolone in an amount of from 0.4 to 0.5 g
    b) soybean oil in an amount of from 15 to 20 g
    c) water for injection
    d) glycerol to give isotonicity of the final composition.

7. A method for anesthetizing a patient in need thereof, comprising intravenously administering an anesthetic effective amount of the composition of claim 1.

8. A composition according to claim 4, comprising, calculated per 100 ml of the final composition:
    a) pregnanolone in an amount of from 0.4 to 0.5 g
    b) soybean oil in an amount of from 15 to 20 g
    c) water for injection
    d) glycerol to give isotonicity of the final composition.

9. A composition according to claim 5, comprising, calculated per 100 ml of the final composition:
    a) pregnanolone in an amount of from 0.4 to 0.5 g
    b) soybean oil in an amount of from 15 to 20 g
    c) water for injection
    d) glycerol to give isotonicity of the final composition.

10. "A method for anesthetizing a patient in need thereof, comprising intravenously administering an anesthetic effective amount of the composition of claim 4."

11. "A method for anesthetizing a patient in need thereof, comprising intravenously administering an anesthetic effective amount of the composition of claim 5."

12. "A method for anesthetizing a patient in need thereof, comprising intravenously administering an anesthetic effective amount of the composition of claim 6."

13. The composition of claim 1 that contains 0.3 to 0.8 grams of pregnanolone per 100 ml of the final composition.

14. The composition of claim 1 that contains 0.4 to 0.5 grams of pregnanolone per 100 ml of the final composition.

* * * * *